United States Patent [19]

Kocal

[11] Patent Number: 5,196,574
[45] Date of Patent: Mar. 23, 1993

[54] DETERGENT ALKYLATION PROCESS USING A FLUORIDED SILICA-ALUMINA

[75] Inventor: Joseph A. Kocal, Gurnee, Ill.

[73] Assignee: UOP, Des Plaines, Ill.

[21] Appl. No.: 816,341

[22] Filed: Dec. 23, 1991

[51] Int. Cl.$^5$ .................... C11D 1/12; C11D 1/755
[52] U.S. Cl. .................... 562/94; 585/455; 585/456; 252/553; 252/556; 252/558
[58] Field of Search .............. 585/455, 456; 252/553, 252/556, 558; 562/94

[56] References Cited

U.S. PATENT DOCUMENTS

| | | | |
|---|---|---|---|
| 2,620,314 | 12/1952 | Hoekstra | 252/448 |
| 3,169,142 | 2/1965 | Knaggs et al. | 260/457 |
| 3,198,849 | 8/1965 | Ballestra | 260/686 |
| 3,201,487 | 8/1965 | Kovsch et al. | 260/671 |
| 3,328,460 | 6/1967 | Vander Mey | 260/327 |
| 3,330,879 | 7/1967 | Goble et al. | 585/455 |
| 3,427,342 | 2/1969 | Brooks et al. | 260/458 |
| 4,036,875 | 7/1977 | Brostrom | 260/505 S |
| 4,240,978 | 12/1980 | Berg | 260/505 P |
| 4,301,316 | 11/1981 | Smith et al. | 585/455 |
| 4,301,317 | 11/1981 | Young | 585/455 |
| 4,358,628 | 11/1982 | Slaugh | 585/455 |
| 4,870,222 | 9/1989 | Bakas et al. | 585/323 |

FOREIGN PATENT DOCUMENTS 0160145 11/1985 European Pat. Off.
2-237641A 9/1990 Japan.
990744 4/1965 United Kingdom.

OTHER PUBLICATIONS

Kurosaki and Okazaki, *Bull Chem. Soc*, Japan, 63, 2363 (1990).
Kurosaki and Okazaki, *Chemistry Letters*, 589 (1991).
R. A. Myers, "Petroleum Refining Processes", 4-36 to 4-38, (McGraw-Hill Book Company), 1986.

*Primary Examiner*—Patrick P. Garvin
*Assistant Examiner*—E. D. Irzinski
*Attorney, Agent, or Firm*—Thomas K. McBride; Eugene I. Snyder

[57] ABSTRACT

A fluorided silca-alumina catalyst, particularly one with a silica:alumina ratio in the range of 1:1-9:1 containing from 1 to 6 weight percent fluoride, is particularly effective in the liquid phase alkylation of benzene to produce linear alkyl benzenes at temperatures no greater than 140° C. Conversions in excess of 98% with selectivity exceeding 85% and linearity exceeding 90% may be achieved readily.

15 Claims, No Drawings

DETERGENT ALKYLATION PROCESS USING A FLUORIDED SILICA-ALUMINA

BACKGROUND OF THE INVENTION

Over fifty years ago it was recognized that alkylbenzene sulfonates (ABS) were quite effective detergents superior to natural soaps in many respects. Because of their lower price, their price stability, and their effectiveness in a wide range of detergent formulations, ABS rapidly displaced soaps in household laundry and dishwashing applications and became the standard surfactants for the detergent industry.

The alkylbenzene sulfonates as initially prepared had substantial branching in the alkyl chain. This situation was maintained until the early 1960's when it became apparent that the branched alkyl-based detergents were contributing to the pollution of lakes and streams and forming relatively stable foams. Examination of the problem showed that the branched structure of the alkyl chains was not susceptible to rapid biodegradation and the surfactant properties of the detergent thus persisted for long periods of time. This was not the case earlier when natural soaps were used, because of the rapid biodegradation of the linear chains in natural soaps.

After recognizing the biodegradability of ABS based on alkylation by linear olefins, industry turned its attention to the production of these unbranched olefins and their subsequent use in the production of linear alkyl benzenes. Processes were developed for efficient alkylation of benzene by available feedstocks containing linear olefins, and the production of linear alkyl benzenes (LAB) became another reliable process broadly available to the petroleum and petrochemical industry. It gradually evolved that HF-catalyzed alkylation was particularly effective in LAB production, and an HF-based alkylation process became the industry standard.

With increasing environmental concern came increasing disenchantment with HF as a catalyst and a concomitant need to find a substitute equal or superior to it in all respects. As regards criteria in addition to the price, the extent of conversion effected by the catalyst, the selectivity of monoalkylbenzene formation, and the linearity of alkylbenzenes produced loomed large. At this point the definition of several terms are necessary to adequately understand and appreciate what follows.

Alkylation typically is performed using an excess of benzene relative to olefins. The ideal catalyst would show 100% conversion of olefins using an equal molar proportion of benzene and olefins, but since this is not attained one strives for maximum olefin conversion using a benzene to olefin molar ratio up to about 30. The better the catalyst, the lower will be the benzene:olefin ratio at a high conversion of, say, 98%. The degree of conversion at a constant value of benzene-olefin ratio is a measure of catalytic activity (subject to the caveat that the ratio must not be so high that the degree of conversion is invariant to small changes in this ratio). The degree of conversion may be expressed by the formula, $$V = \frac{C}{T} \times 100,$$

where V equals percent conversion, C equals moles of olefin consumed, and T equals moles olefin initially present.

However active the catalyst may be, it is not valuable unless it also is selective. Selectivity is defined as the percentage of total olefin consumed under reaction conditions which appears as monoalkylbenzene and can be expressed by the equation, $$S = \frac{M}{C} \times 100,$$

where S equals selectivity, M equals moles of monoalkylbenzenes produced, and C equals moles olefin consumed. The better the selectivity, the more desirable is the catalyst. An approximate measure of selectivity is given by the equation, $$S = \frac{\text{weight monoalkylbenzene}}{\text{weight total products}} \times 100$$

where "total products" includes monoalkylbenzenes, polyalkylbenzenes, and olefin oligomers. At high selectivity (S>85%) the results calculated from the two equations are nearly identical. The latter of the foregoing two equations is routinely used in commercial practice because of the difficulty in distinguishing between oligomers and polyalkylbenzenes.

Finally, the reaction of linear olefins with benzene in principal proceeds according to the equation, $$C_6H_6 + R_1CH=CHR_2 \rightarrow C_6H_5CH(R_1)CH_2R_2 + C_6H_5CH(R_2)CH_2R_1.$$

Note that the side chain is branched solely at the benzylic carbon and contains only one branch in the chain. Although strictly speaking this is not a linear alkylbenzene, nonetheless the terminology which has grown up around the process and product in fact includes as linear alkylbenzenes those materials whose alkyl group chemically arises directly from linear olefins and therefore includes alpha-branched olefins. Because alkylation catalysts also may induce the rearrangement of olefins to give products which are not readily biodegradable (vide supra), for example, $\alpha,\alpha$-disubstituted olefins which subsequently react with benzene to afford an alkyl benzene with branching at other than the benzylic carbon, $$R_1CH=CHR_2 \longrightarrow R_1CH=C(R_3)R_4 \xrightarrow{C_6H_6}$$

$$C_6H_5CH(R_1)CH(R_3)R_4$$

the degree to which the catalyst effects formation of linear alkyl benzenes is another important catalyst parameter. The degree of linearity can be expressed by the equation, $$D = \frac{L}{M} \times 100,$$

where D equals degree of linearity, L equals moles of linear monoalkyl benzene produced, and M equals moles of monoalkyl benzene produced.

Consequently, the ideal catalyst is one where V equals 100, S equals 100, and D equals 100. The minimum requirement is that linearity be at least 90% at a selectivity of at least 85% and at a conversion of at least 98%. These are minimum requirements; that is, if a catalyst fails to meet all of the foregoing requirements simultaneously the catalyst is commercially unacceptable.

The linearity requirement is assuming added importance and significance in view of the expectation in some areas of minimum standards for linearity in detergents of 92–95% near-term, increasing to 95–98% by about the year 2000. Since the olefinic feedstock used for alkylation generally contains a small percentage of non-linear olefins—a non-line olefin content of about 2% is common to many processes—the requisite linearity in the detergent alkylate places even more stringent requirements on catalytic performance; the inherent linearity of the alkylation process must increase by the amount of non-linear olefins present in the feedstock. For example, with a feedstock containing 2% non-linear olefins the catalyst must effect alkylation with 92% linearity in order to afford a product with 90% linearity, and with a feedstock containing 4% non-linear olefins the catalyst must effect alkylation with 94% linearity to achieve the same result.

Our solution to the problem of identifying a catalyst for detergent alkylation which satisfies all the aforementioned criteria, and which in particular meets the increasingly stringent requirements of linearity, arose from our observation that the isomerization of linear olefins to non-linear olefins—this is the process ultimately responsible for non-linear detergent alkylate arising from a linear olefin feedstock—is quite sensitive to temperature but relatively insensitive to the particular candidate catalyst for the detergent alkylate process. This result was itself quite surprising, but more importantly it suggested that effecting alkylation at a lower temperature was the key to greater product linearity. Our focus then shifted to finding more active catalysts, i.e., materials which would catalyze detergent alkylation at lower temperatures.

The importance of our observation that temperature is the major factor in olefin isomerization and that the particular catalyst plays only a minor role cannot be overemphasized, for it permits one to focus solely on methods of reducing the alkylation temperature. Since the other requisites of a detergent alkylation process can be addressed in other ways, our observation significantly foreshortens the focus on ways to obtain an improved process. A result of our observation is the novel use of a solid acid catalyst to craft a new process permitting alkylation at a substantially lower temperature than that previously attainable using other members of this class of catalysts.

The use of silica-aluminas as a support for various metals in the alkylation of aromatics with olefins is reasonably well known. For example, U.S. Pat. No. 3,169,999 teaches a catalyst consisting essentially of small amounts of nickel and chromia on a silica-alumina support, and U.S. Pat. No. 3,201,487 teaches 25–50 weight percent chromia on a silica-alumina support, both for alkylation of aromatics by olefins. Crystalline aluminosilicates as catalysts in detergent alkylation has been described in U.S. Pat. Nos. 4,301,317 and 4,301,316. U.S. Pat. No. 4,358,628 claims an alkylation process with an olefin using as a catalyst tungsten oxide supported on a porous silica-alumina support containing 70–90% silica prepared in a very particular way.

More relevant is European Patent Application 0160145 which teaches as a catalyst in detergent alkylation an amorphous silica-alumina having specified channels or networks of pores and with at least 10% of the cationic sites occupied by ions other than alkali or alkaline earth metals. Even more relevant is U.S. Pat. No. 4,870,222 where the patentees teach that amorphous silica-alumina is the most preferred catalyst for alkylation in a process for the production of a monoalkylated aromatic compound in which an aromatic is first alkylated, the product mixture is separated, and the polyalkylated material thereafter is transalkylated.

There appears to be few references to fluorided silica-aluminas in the literature. Japanese patent application J02237641-A refers to a silica-alumina (20% silica) which was contacted at 400° C. with $CCIF_3$ to afford a catalyst containing 28% fluorine as having a higher activity and a longer operating life in cumene production by vapor phase alkylation of benzene. Kurosaki and Okazaki [*Bull Chem. Soc. Japan*, 63, 2363 (1990)] describe a silica:alumina (6.7:1) modified by vapor-phase fluorination with $CCIF_3$ at 350°–550° C. in the alkylation of benzene with propylene. Cf. Kurosaki and Okazaki, *Chemistry Letters*, 589 (1991). However, in none of the prior art is there recognition of the benefits of a fluoride silica-alumina to afford higher linearity in the products resulting from the detergent alkylation process, especially as to a silica-alumina prepared by the method described within and containing the fluorine levels which we have found effective.

SUMMARY OF THE INVENTION

The object of this invention is to prepare linear alkylbenzenes by the alkylation of benzene with an olefin, particularly in a continuous manner, where alkylation proceeds with at least 98% conversion of olefin, at least 85% selectivity of olefin conversion to monoalkylbenzenes, and with at least 90% linearity with respect to monoalkylbenzene formation. In an embodiment benzene in a total of from 5 to about 30 molar proportions is reacted with 1 molar proportion of a linear monoolefin, or a mixture of linear monoolefins, in the presence of a catalyst consisting essentially of a fluorided silica-alumina, where the weight ratio of silica to alumina is from about 1:1 to about 9:1. In a more specific embodiment the linear monoolefins have from 6 up to about 20 carbon atoms. In a still more specific embodiment the molar proportion of total benzene relative to total linear monoolefins is from about 8:1 to about 20:1. Other embodiments will be apparent from the ensuing description.

DESCRIPTION OF THE INVENTION

In our search for catalysts in a detergent alkylation process, and especially solid catalysts capable of being used as a bed in a continuous fixed bed detergent alkylation process, it soon became clear that the degree of branching in the alkyl chain of the resulting alkylbenzene (detergent alkylate) was principally a function of temperature, with lower reaction temperatures affording lower branching. Since linearity of the alkyl chain is an increasingly important environmental and regulatory consideration, our observation led to a search for catalysts which would effect alkylation in a continuous process at acceptable productivity rates and at a temperature not exceeding 140° C. For the purpose of this application an acceptable productivity means an olefin liquid hourly space velocity of at least 0.05 hr$^{-1}$. What we have found is that fluoridation of silica-aluminas affords a substantial activity increase over the non-fluorided material, at least over a certain compositional range of silica-aluminas. As described in more detail within, silica-aluminas originally containing between 50 and 90 weight percent silica and which in the finished product contain from 1 to 6 weight percent fluorine, calculated as fluoride, are quite suitable catalysts for a detergent alkylation process at temperatures not exceeding 140° C. and effect detergent alkylation with at least 98% conversion while simultaneously affording at least 85% selectivity to monoalkylbenzenes with at least 90% linearity of the alkyl side chain.

The feedstocks which are used in the practice of this invention normally result from the dehydrogenation of paraffins. The entire dehydrogenation reaction mixture often is used with the dehydrogenation reaction not being run to completion to minimize cracking, isomerization, and other undesirable and deleterious byproducts. The branched olefins which are formed in dehydrogenation are not removed, yet the total amount of nonlinear alkylbenzene formed still must be sufficiently small that the monoalkylate meets the requirements of 90% linearity. The polyolefins formed during dehydrogenation are minimized in the feedstocks used in the practice of this invention. Consequently the feedstocks are a mixture largely of unreacted paraffins, small amounts (ca. 2%) of branched olefins, and unbranched, linear monoolefins which typically are in the C6-C20 range, although those in the C8-C16 range are preferred in the practice of this invention, and those in the C10-C14 range are even more preferred. Unsaturation may appear anywhere on the linear monoolefin chain; there is no requirement as to the position of the double bond, but only a requirement as to the linearity of the olefin. See R. A. Myers, "Petroleum Refining Processes", 4-36 to 4-38. (McGraw-Hill Book Company), 1986.

The linear monoolefins in the feedstock are reacted with benzene. Although the stoichiometry of the alkylation reaction requires only 1 molar proportion of benzene per mole of total linear monoolefins, the use of a 1:1 mole proportion results in excessive olefin polymerization and polyalkylation. That is, the reaction product under such conditions would consist not only of the desired monoalkylbenzenes, but also large amounts of the dialkylbenzenes, trialkylbenzenes, possibly higher polyalkylated benzenes, olefin dimers, trimers, etc., and unreacted benzene. On the other hand, it is desired to have the benzene:olefin molar ratio as close to 1:1 as possible to maximize benzene utilization and to minimize the recycle of unreacted benzene. The actual molar proportion of benzene to total monoolefins will therefore have an important effect on both conversion and, perhaps more importantly, selectivity of the alkylation reaction. In order to carry out alkylation with the conversion, selectivity, and linearity required using the catalysts of our process, a total benzene:linear monoolefin molar ratio of from 5:1 up to as high as 30:1 is recommended, although the process normally operates satisfactorily at a total benzene:linear monoolefins molar ratio between about 8:1 and about 20:1.

The benzene and linear monoolefins are reacted in the presence of a catalyst under alkylation conditions. These alkylation conditions include a temperature in the range between about 80° C. and 140° C., most usually at a temperature not exceeding 135° C. Since the alkylation is conducted as a liquid phase process, pressures must be sufficient to maintain the reactants in the liquid state. The requisite pressure necessarily depends upon the feedstock and temperature, but normally is in the range of 200-1000 psig (1379-6895 kPa), and most usually 300-500 psig (2069-3448 kPa).

The alkylation of benzene by linear monoolefins with the requisite conversion, selectivity, and linearity is effected by fluorided silica-aluminas containing a weight ratio of silica to alumina of at least 1:1 (50 weight percent) up to as high as 9:1 (90 weight percent). The stated range is a useful compromise between selectivity and activity. Selectivity of the fluorided silica-aluminas of this invention increases with increasing silica content, which recommends or suggests the use of as high a silica level as possible. However, the activity of the fluorided materials increases initially, appears to pass through a maximum at about a 3:1 ratio of silica:alumina, and then decreases thereafter. Accordingly, although fluorided silica-aluminas can be used throughout the given range, those having a silica to alumina weight ratio between about 65:35 and 85:15 are preferred in the practice of my invention.

Preferred catalysts contain from about 1 up to 6 weight percent fluoride based on volatile-free finished silica-alumina catalyst. Higher fluoride levels may be used but without any substantial incremental benefit. The preferred fluoride level depends on the silica-alumina ratio. For example, for a 75:25 silica:alumina ratio fluoride levels between about 1.5 and 3.5 are preferred.

An amorphous, cogelled, oil-dropped silica-alumina is preferred for the successful practice of this invention. Other silica-aluminas of the same apparent composition may be used, but generally are inferior to the amorphous, cogelled, oil-dropped product. The oil-drop method of preparing, for example, aluminas is an old, tried and true method dating to U.S. Pat. No. 2,620,314, and therefore will not here be discussed in great detail. The following description will be familiar to one practicing this art and will serve as a general description of the subject method.

The cogelled silica-alumina composition is suitably prepared as spheroidal particles by the well-known oil-drop method. In a preferred method of manufacture, an alumina sol, utilized as an alumina source, is commingled with an acidified water glass solution as a silica source, and the mixture is further commingled with a suitable gelling agent, for example, urea, hexamethylenetetramine (HMT), or mixtures thereof. The mixture is discharged while still below gelation temperature by means of a nozzle or rotating disk, into a hot oil bath maintained at or above gelation temperature. The mixture is dispersed into the hot oil bath as droplets which form into spherical gel particles. The alumina sol is preferably prepared by a method wherein aluminum pellets are commingled with a quantity of treated or deionized water, with hydrochloric acid being added thereto in a sufficient amount to digest a portion of the aluminum metal and form the desired sol. A suitable reaction rate is effected at about reflux temperature of the mixture.

The spheroidal gel particles prepared by the oil-drop method are aged, usually in the oil bath, for a period of at least 10-16 hours, and then in a suitable alkaline or basic medium for at least 3 to about 10 hours, and finally water washed. Proper gelation of the mixture in the oil bath, as well as subsequent aging of the gel spheres, is not readily accomplished below about 50° C., and at about 100° C., the rapid evolution of the gases tend to rupture and otherwise weaken the spheres. By maintaining sufficient superatmospheric pressure during the forming and aging steps in order to maintain water in the liquid phase, a higher aging temperature may be employed, frequently with improved results. If the gel particles are aged at superatmospheric pressure, no alkaline aging step is required.

The spheres are water-washed, preferably with water containing a small amount of ammonium hydroxide and/or ammonium nitrate. After washing, the spheres are dried, at a temperature from about 85°–250° C. for a period from about 6 to about 24 hours or more, and then calcined at a temperature from about 300°–760° C. for a period from about 2 to about 12 hours or more.

The fluorided silica-alumina catalysts of this invention are prepared by impregnating the silica-alumina with essentially hydrogen fluoride. This is not to say that HF is the only fluoride source, but rather that the fluoride source is equivalent to HF in affording a fluorided silica-alumina free of additional metals or metallic species and which analytically contains only additional HF. Examples of a suitable fluoride source, in addition to HF, include ammonium fluoride [$NH_4F$], ammonium bifluoride [$NH_4HF_2$], and organic fluorides. When an ammonium fluoride is used $NH_3$ is volatilized during subsequent heating of the fluoride-impregnated silica-alumina. When organic fluorides are used the impregnated silica-alumina is subsequently heated under conditions which oxidize carbon to carbon dioxide and excess hydrogen to water, both of which volatilize to leave the equivalent of an HF-impregnated product.

The preparation of the fluorided silica-alumina catalyst may be performed by a variety of procedures, depending upon the fluoride source, fluoride level sought, and so forth. For example, when an ammonium fluoride is used equal volumes of the silica-alumina and an aqueous solution of the ammonium fluoride containing the desired amount of fluoride are intimately mixed, (e.g., cold rolled) and the mixture subsequently heated to evaporate the water. The resulting fluoride-impregnated product may be dried at 125°–175° C. for several hours, and then calcined at a temperature typically in the 350°–550° C. range for 1–6 hours, depending on the temperature used. For calcination near 400° C. the time generally is about 3 hours. It is found that ammonia is lost from the catalyst when the impregnated material is heated to about 150° C. No significant amounts of fluoride are lost up to a temperature of about 550° C., but fluoride loss is observed at higher temperatures.

When HF is the fluoride source a similar impregnation method may be used, although it also is possible to fluoride the catalyst with a gaseous HF stream. In the latter instance no drying step is necessary and the fluorided material may be calcined directly. Where an organic fluoride is used, the silica-alumina may be impregnated using either a vapor phase or liquid phase source of fluoride. For example, an organic fluoride such as t-butyl fluoride can be impregnated from its solution in a volatile solvent, the solvent subsequently removed by evaporation, the silica-alumina heated to remove the last traces of solvent and then calcined to remove the organic material. This procedure is similar to impregnation using inorganic fluoride but may suffer from fluoride loss on calcination. Alternatively, the t-butyl fluoride may be volatilized, and HF deposited on the silica-alumina via thermal decomposition of the t-butyl fluoride. Fluoride levels can be controlled by gas rate, time and temperature of exposure.

It has been found that the catalysts of my invention are quite sensitive to water. Thus it is desirable that the feedstocks be dried to a level of 1 ppm or less. With increasing feedstock water content the catalysts are found to deactivate. It also is quite desirable to dry the catalyst thoroughly immediately prior to use. This can be successfully done by heating my catalysts in a dry, unreactive gas such as air or nitrogen at a temperature of at least 150° C., but preferably at even higher temperatures. The time needed for adequate drying will depend on such factors as gas flow rate and temperature, but at 300° C. a time from 6 to about 12 hours appears adequate.

Alkylation of benzene by the linear monoolefins of this invention may be conducted either as a batch method or in a continuous manner, although the latter is greatly preferred and therefore will be described in some detail. Fluorided silica-alumina catalyst may be used as a packed bed or a fluidized bed. Feedstock to the reaction zone may be passed either upflow or downflow, or even horizontally as in a radial bed reactor. The admixture of benzene and the feedstock containing the total linear monoolefins is introduced at a total benzene:olefin ratio of between 5:1 and 30:1, although usually the ratio is in the range between about 8:1 and 20:1. In one desirable variant olefin may be fed into several discrete points within the reaction zone, and at each zone the benzene:olefin ratio may be greater than 30:1. However, the total benzene:olefin ratio used in the foregoing variant of my invention still will be within the stated range. The total feed mixture, that is, benzene plus feedstock containing linear monoolefins, is passed through the packed bed at a liquid hourly space velocity (LHSV) between about 0.3 and about 6 $hr^{-1}$ depending upon alkylation temperature, how long the catalyst has been used, the ratio of silica to alumina and fluoride level in the catalyst, and so on. The temperature in the reaction zone will be maintained at between about 80° and about 140° C., and pressures generally will vary between about 200 and about 1000 psig (1379–6895 kPa) to ensure a liquid phase alkylation. After passage of the benzene and linear monoolefin feedstock through the reaction zone, the effluent is collected and separated into benzene, which is recycled to the feed end of the reaction zone, paraffin, which is recycled to the dehydrogenation unit, and alkylated benzenes. The alkylated benzenes are usually further separated into the monoalkyl benzenes, used in subsequent suffonation to prepare the linear alkylbenzene sulfonates, and the oligomers plus polyalkylbenzenes. Since the reaction goes to at least 98% conversion, little unreacted monoolefin is recycled with paraffin.

When alkylation of the aromatics, especially of benzene, is performed with monoolefins having from about 6 to about 20 carbon atoms, more usually from about 8 to about 16 carbon atoms, and even more particularly having between about 10 and about 14 carbon atoms, the resulting mixture of monoalkylated aromatic compounds commonly is referred to as detergent alkylate. The reason for such an assignation is rather simple; the major use of such a product is as a feedstock for the preparation of detergents by sulfonation of the feedstock and subsequent conversion of the sulfonic acids, particularly the monosulfonic acids, to salts which function as anionic surfactants.

Sulfonation of detergent alkylate may be effected by numerous agents including sulfuric acid, mixtures of sulfuric acid and sulfur trioxide, which are known variously as fuming sulfuric acid and oleum, sulfur trioxide, and to a lesser extent chlorosulfonic acid, ClSO$_3$H, which sometimes is known as chlorosulfuric acid. An advantage of using sulfuric acid as the sulfonating agent is its convenience and low cost. However, because the sulfonation of the aromatic ring with sulfuric acid produces water, which dilutes the sulfuric acid used as the sulfonating agent and substantially reduces its activity, it requires perhaps 3-4 molar proportions of sulfuric acid per mole of aromatic compound to effect a suitably high conversion. Another disadvantage of the use of sulfuric acid as the sulfonating agent is the need to recover spent sulfuric acid from a diluted sulfuric acid solution.

The use of fuming sulfuric acid obviates many of the foregoing problems. In particular, by using mixtures of sulfur trioxide and sulfuric one can effect reaction preferentially with the sulfur trioxide, a reaction which does not lead to the production of water. Consequently, spent acid formation is reduced and a relatively lower molar proportion of reagent is required than is the case for sulfuric acid alone. The extent of dilution of sulfuric acid is far less than in the case where sulfuric acid alone is the sulfonating agent, and sulfuric acid recovery is consequently facilitated.

In recent years sulfur trioxide has become the sulfonating reagent of choice. As previously mentioned, its reaction with the aromatic ring does not afford water as a byproduct, and because of its extreme reactivity very little excess of sulfur trioxide relative to the aromatic ring to be sulfonated is required. Many commercial processes, some of which are described in more detail below, use gaseous sulfur trioxide diluted with an inert and dry gas, often air, to afford a sulfonating mixture generally containing no more than 20 volume percent sulfur trioxide. Dilution of sulfur trioxide is desirable to moderate the reaction between this extremely energetic sulfonating agent and the aromatic. The extreme reactivity of sulfur trioxide also may be moderated by complexing it with Lewis bases such as amines, dioxane, dimethylformamide, dimethylsulfoxide, and so on. Although the use of chlorosulfonic acid as the sulfonating agent in principle may be quite advantageous, the formation of hydrogen chloride as a byproduct has diminished its luster as a sulfonating agent, especially with the advent of numerous processes employing sulfur trioxide.

Sulfonation conditions will, of course, depend on the sulfonating agent used but are reasonably well known to those practicing the art. When 100% sulfuric acid is used as a sulfonating agent reaction temperatures often are on the order of 45°-55° C. and enough sulfuric acid is used to afford generally a large molar excess, the sulfuric acid being used in as much as about 4 molar proportions and as little as perhaps 1.5 molar proportions relative to the detergent alkylate. Even with sulfuric acid the reaction is quite exothermic and the reaction mixture needs to be continually cooled to maintain the temperature within the desired limits. When fuming sulfuric acid is used a mixture containing between 20-30% sulfur trioxide is generally favored at a reaction temperature typically between about 30° and 45° C. The reaction time generally is short, on the order of several minutes, and the molar proportion of oleum may be as little as about 1.1 for every mole of detergent alkylate. As with sulfuric acid, spent acid is formed when fuming sulfuric acid is used as the sulfonating agent. Generally this is separated simple by diluting the sulfonation mixture with water, with strong cooling necessitated by the high exothermicity of dilution. The water insoluble monosulfonation products settle as an oil soluble water immiscible layer which then may be withdrawn, and sulfuric acid can be subsequently recovered from the aqueous phase.

As previously noted, an advantage of using sulfur trioxide as the sulfonation agent is that no water is produced and therefore no spent sulfuric acid needs to be recovered. The most commonly employed method of using sulfur trioxide is as a vapor diluted with an inert, dry carrier gas, usually air, to give a dilute sulfur trioxide gas stream most often containing between about 2 and 20 volume percent sulfur trioxide. Sulfonation with sulfur trioxide is most often performed in the temperature range of between about 25° and 120° C., although more usually the reaction temperature is kept under 100° C., and a preferred temperature range is in the interval from 30° to about 75° C. Dilution of the sulfur trioxide vapor also may be obtained, in effect, by carrying out the sulfonation at reduced pressure. Only a slight excess of sulfur trioxide relative to detergent alkylate is required, and typically the ratio of sulfur trioxide to alkylate is on the order of 1.05:1 to 1.2:1.

A relatively large number of processes have been developed for sulfonation of detergent alkylation. For example, U.S. Pat. No. 3,169,142 uses a flowing film of the detergent alkylate with a pressurized stream of an inert diluent and a vaporized sulfur trioxide, where the inert diluent may be dry air, nitrogen, carbon dioxide, carbon monoxide, sulfur dioxide, a halogenated hydrocarbon, or a low molecular weight paraffinic hydrocarbon such as methane, ethane, propane, butane, or a mixture thereof. Sulfur trioxide is diluted with a gas within the range of 5:1 to 50:1 by volume and the gas mixture is preheated to the range of 4°-10° C. to ensure that no sulfur trioxide will subsequently be condensed. U.S. Pat. No. 3,328,460 describes sulfonation using a gas mixture of inert gas and gaseous sulfur trioxide where the detergent alkylate is reacted as a liquid film on the order of 0.002-0.003 inch thick at a reaction temperature of about 30° C. U.S. Pat. No. 3,535,339 uses gaseous sulfur trioxide at subatmospheric pressure without a gaseous diluent and also uses a thin flowing film of liquid detergent alkylate for reaction. At another extreme is U.S. Pat. No. 3,198,849, which describes an exothermic sulfonation between an alkylbenzene and undiluted gaseous sulfur trioxide. U.S. Pat. No. 3,427,342 describes the sulfonation of alkylbenzenes using gaseous sulfur trioxide in a mole ratio of 1.05:1 to about 1.15:1. The patentee controls the sulfur dioxide at 2-8% by volume and most preferably uses an 8-10 mole percent excess of sulfur trioxide relative to the alkylbenzene. Although the average temperature in the reaction mixture zone is 30°-55° C., the temperature in the reaction zone, which is only a short portion of the reaction mixture zone, is substantially higher at 66°-93° C.

It often is recommended that the reaction mixture be placed in a digester zone subsequent to leaving the reactor in order to enable further reaction to occur. Reaction of sulfur trioxide with an alkylbenzene also affords sulfonic acid anhydrides which, upon contact with water, would decompose to afford the sulfonic acid and sulfuric acid. However, when a mixture containing unreacted alkylbenzene and sulfonic acid anhydrides is allowed to remain in a digestion zone for a short period after reaction, the sulfonic acid anhydride breaks down by reacting with unreacted alkylbenzene to afford a reaction mixture which is virtually pure sulfonic acids with virtually no unreacted alkylbenzene. Additional references to sulfonation may be found in "Synthetic Detergents", A. P. Davidsohn and B. M. Milwidsky, George Godwin Ltd. (London), 1978 and "Detergent Manufacture", Chemical Technology Review 62, Noyes Data Corporation (Park Ridge, N.J., U.S.A.), 1981.

After sulfonation the resulting mixture of alkylbenzene sulfonic acids is neutralized to form a sodium and/or, to a much lesser extent, other alkali metal salts. This usually is effected by reacting the alkylbenzene sulfonic acid with a suitable aqueous base of the alkali metal, such as the alkali metal hydroxide or alkali metal carbonate. The alkylbenzene sulfonic acid mixture from sulfonation of the detergent alkylates is neutralized by passage of the material into a saponification zone where the sulfonation reaction mixture is mixed with an aqueous stream containing ammonia, sodium hydroxide, or potassium hydroxide. Neutralization with, for example, sodium hydroxide affords the sodium alkyl aromatic monosulfonate salt. The neutralization product is used directly, as for an enhanced oil recovery surfactant, or it can be subjected to separation steps to obtain a higher purity of the desired product. For example, it is common practice to pass such a mixture into an extraction zone where the sulfonates are extracted from unreacted hydrocarbonaceous material with an aqueous mixture of an alkyl alcohol, with 25-60 weight percent isopropyl alcohol preferred as the solvent. The isopropyl alcohol solution then can be easily stripped from the extract stream to yield the purified sulfonates. See U.S. Pat. Nos. 4,036,875 and 4,240,978.

The following examples are illustrative only. They show in some detail how the invention claimed below may be carried out but are not intended to limit the invention in any way.

EXAMPLES

General Procedure. Catalyst was packed in a bed 0.5 inch in diameter and 8 inches long equipped with a sliding thermocouple to survey bed temperature at various depths. The feedstock containing linear monoolefins resulted from dehydrogenation of n-paraffins and had the composition given below.

TABLE 1

| Feedstock Composition (weight percent) | |
|---|---|
| Branched hydrocarbons | 7.9 |
| Unbranched hydrocarbons | 92.1 |
| | Alkenes / Alkanes |
| C9 | <0.1 / 0.1 |
| C10 | 0.9 / 7.9 |

TABLE 1-continued

| Feedstock Composition (weight percent) | | |
|---|---|---|
| C11 | 4.1 | 31.8 |
| C12 | 3.6 | 24.8 |
| C13 | 2.6 | 15.7 |
| C14 | 0.1 | 0.4 |
| Total | 11.3 | 80.7 |

The feedstock containing the linear monoolefins and benzene at a molar ratio of 15:1 benzene:olefin was fed upflow to the packed bed of catalyst at conditions given in the table. Effluent was analyzed by gas chromatography. Analyses were performed after the reactor had lined out, that is, after equilibrium had been attained.

All silica-alumina catalysts were prepared as 1/16-inch diameter spheres by the oil-dropping method and were fluorided by impregnation with an aqueous solution of ammonium bifluoride containing the desired amount of fluoride. The fluoride-impregnated material was dried at ca. 150° C., then calcined in air at 400° C. for 3 hours, to afford the catalysts listed below. The clay was a montmorillonite clay commercially available as Filtrol 24.

| Catalyst Designation | $SiO_2/Al_2O_3$ | Nominal wt. % F |
|---|---|---|
| A | 90/10 | 0 |
| B | 90/10 | 1.00 |
| C | 90/10 | 1.75 |
| D | 90/10 | 2.50 |
| E | 75/25 | 0 |
| F | 75/25 | 1.75 |
| G | 75/25 | 2.50 |
| H | 75/25 | 3.00 |
| I | 75/25 | 4.00 |
| J | Clay | 0 |

EXAMPLE 1

Reactions of 1-decene. The unfluorided silica-aluminas, (catalysts A and E) montmorillonite clay (catalyst J), and a fluorided silica-alumina (catalyst G) were evaluated for their effect on 1-decene in the absence of benzene by passing a stream of 1-decene in n-decane as a solvent (1:10 weight ratio) over a bed of catalyst at 135° and 150° C. at 500 psig and an LHSV of 2 hr$^{-1}$. Effluent was analyzed for dimer, trimer, cracked products, and methylnonenes. The latter arise from isomerization of and alkyl group migration in 1-decene and can be taken as a measure of the propensity of the catalysts to make non-linear alkylate during alkylation of benzene by 1-decene. Results are given in Table 1.

TABLE 1

| | Conversion of 1-Decene in Absence of Benzene | | | | | | | |
|---|---|---|---|---|---|---|---|---|
| | Catalyst | | | | | | | |
| | A | | E | | G | | J | |
| Temp, °C. | 150 | 135 | 150 | 135 | 150 | 135 | 150 | 135 |
| % Conversion | 20 | 13 | 31 | 22 | 46 | 32 | 41 | 28 |
| Selectivity, wt. % | | | | | | | | |
| Dimer | 62.5 | 69.2 | 63.3 | 64.3 | 60.1 | 62.6 | 63.2 | 64.2 |
| Trimer | 9.0 | 14.6 | 13.1 | 19.4 | 20.1 | 23.4 | 23.0 | 26.5 |
| Light[a] Ends | 25.0 | 15.3 | 21.3 | 15.1 | 17.2 | 12.6 | 12.0 | 8.3 |
| Me-C9=[b] | 3.5 | 0.9 | 2.3 | 1.2 | 2.6 | 1.4 | 1.8 | 1.0 |
| YIELD, MeC9=[c] | .70 | .12 | .71 | .26 | 1.20 | .45 | .74 | .28 |

[a]Cracked products.
[b]Methylnonenes (branched olefins)
[c]Absolute yield (%) methylnonenes (conversion × selectivity)

Insofar as conversion is related to catalyst activity, the data show clearly that the fluorided silica-alumina is the most active catalyst, and that fluoridation has a profound effect on activity. However, the selectivity of silica-aluminas to branched olefin production is only slightly changed by fluoridation. Furthermore, branch olefin production is reduced considerably—by about 50% or more—upon reducing the temperature from 150° to 135° C. What these data show rather poignantly is that the extent of branched olefin production is far more sensitive to temperature than to the particular catalyst tested. This is also seen in the last row of the table, where branched olefin yield is seen to decrease by about a third or more in reducing the temperature from 150° to 135° C. thus, one can confidently extrapolate from these data that decreasing the alkylation temperature of benzene by linear olefins will afford less branched alkylate, regardless of the catalyst.

Another way of looking at these data is to compare the extent of branched olefin production at the same olefin conversion. Insofar as percent olefin conversion can be correlated with the degree of benzene conversion during alkylation, differences in selectivity of branched olefin formation are a measure of expected differences in the non-linearity of alkylate. Table 1 shows that at about 30% 1-decene conversion fluorided silica (G) affords much less branched olefin than its non-fluorided counterpart (E). Presumably this also would hold for catalyst A, although a temperature near 170° C. would be required for 30% 1-decene conversion.

What is clear and unambiguous from the foregoing data is that fluorided silica-alumina is superior to its non-fluorided counterpart in not effecting branching at conditions giving comparable catalyst activity.

EXAMPLE 2

Alkylation of benzene with 1-decene. Catalyst G was used as a fixed bed to effect the alkylation of benzene by 1-decene, using a feedstock with a benzene:olefin ratio of 25:1, at 500 psig and LHSV of 2 hr$^{-1}$. Table 2 shows results at two temperatures.

TABLE 2

Alkylation of Benzene with 1-Decene using Catalyst G.

| Temperature, °C. | 120 | 100 |
|---|---|---|
| Olefin Conversion, % | 100 | 100 |
| % Linearity | 95.5 | 97.8 |
| % Methyl Branched | 2.90 | 0.45 |

These data show that temperature has a profound effect on both the extent of linearity and methyl branching in the alkylate. In particular, the extent of methyl branching in the non-linear alkylate decreases from 64% (2.9/4.5) at 120° to 20% (0.45/2.2) at 100° C. We also interpret this data to mean there is a pre-reaction isomerization of 1-decene to form methyl-branched olefins which subsequently alkylate benzene. Once more the data point strongly toward modifying the catalyst to increase alkylation activity so as to permit lower operating temperatures.

EXAMPLE 3

Alkylation of benzene with mixed olefin feedstock; temperature effect on linearity. The feedstock previously described was used as the olefins source for alkylation at a benzene:olefin ration of 25:1 at 500 psig and a LHSV of 2 hr$^{-1}$ using various catalysts, as summarized in Table 3.

TABLE 3

Effect of Temperature on Linearity of Alkylate

| | Catalyst | | | | | | | | |
|---|---|---|---|---|---|---|---|---|---|
| | E | | | G | | | J | | |
| % Conversion | 100 | 95 | 70 | 100 | 100 | 100 | 100 | 96 | 72 |
| Temp., °C. | 150 | 135 | 120 | 150 | 135 | 120 | 150 | 135 | 120 |
| % Linearity | 90.2 | 92.1 | 93.4 | 90.0 | 92.5 | 93.6 | 92.1 | 93.5 | 94.9 |

The foregoing data show that the detergent alkylate formed at any given temperature has the same percent linearity, whether or not the silica is fluorided (cf. results of E and G). However, the clay affords a detergent alkylate with somewhat higher linearity, especially at the higher temperature. What distinguishes the fluorided silica-alumina (G) from the other catalysts is its increased activity, for G leads to 100% conversion even at 120° C., whereas the other two catalysts give only about 70% conversion at that temperature. This constitutes a striking example of the advantage of using a fluorided silica-alumina catalyst. More particularly, note that the linearity of alkylate formed at 120° C. using G is the same as that formed at 135° C. using J, but under these conditions G still brings about 100% conversion whereas J does not.

EXAMPLE 4

Effect of fluoride level on silica-alumina catalysts. Alkylation of benzene was performed at 135° C., 500 psig, LHSV of 2 hr$^{-1}$, and a benzene: olefin ratio of 25:1, with the results shown in Table 4. The 75:25 silica-alumina having 2.5% fluoride seemed to have the highest activity, is measured by its having the highest number of hours at 100% conversion. Also note again that the percent linearity is, except for the unfluorided 90:10 silica-alumina, essentially independent of the catalyst.

TABLE 4

Effect of Fluoride Level on Silica-alumina Catalyst Performance.

| | Catalyst | | | | | | | | |
|---|---|---|---|---|---|---|---|---|---|
| | A | B | C | D | E | F | G | H | I |
| Hours at 100% Conv. | 18 | 24 | 32 | 44 | 20 | 32 | 48 | 45 | 41 |
| % Linearity | 91.2 | 92.2 | 92.6 | 92.5 | 92.2 | 92.4 | 92.6 | 92.3 | 92.3 |
| % Selectivity | 91.1 | 92.1 | 91.8 | 91.7 | 90.3 | 90.5 | 91.5 | 90.9 | 90.8 |

What is claimed is:

1. A method for alkylating benzene with one or more linear monoolefins having from about 6 to about 20 carbon atoms with at least 98% conversion of olefins, at least 85% selectivity of olefin conversion to monoalkylbenzenes, and with at least 90% linearity with respect to monoalkylbenzene formation comprising reacting benzene with the linear monoolefins in a feedstock at alkylating conditions and in the presence of a catalyst, said feedstock containing at least one linear monoolefin, said alkylating conditions including reacting from about 5 to about 30 molar proportions of total benzene for each molar proportion of total linear monoolefins at a temperature from about 80° C. to about 140° C. and a pressure from about 200 to about 1000 psig, where the catalyst is a fluorided silica-alumina having a silica:alumina weight ratio of from about 1:1 to about 9:1 and contains from about 1 to about 6 weight percent fluoride.

2. The method of claim 1 where the molar ratio of benzene to linear monoolefins is from about 8 to about 20.

3. The method of claim 1 where the temperature does not exceed 135° C.

4. The method of claim 1 where the monoolefins have from about 8 to about 16 carbon atoms.

5. The method of claim 4 where the monoolefins have from about 10 to about 14 carbon atoms.

6. The method of claim 1 where the catalyst has a silica to alumina weight ratio of from 65:35 to about 85:15.

7. The method of claim 1 where the catalyst contains from 1.5 to about 3.5 weight percent fluoride.

8. A process for the production of a biodegradable detergent alkylbenzene sulfonate which comprises: alkylating benzene with at least one linear monoolefin containing from 6 to about 20 carbon atoms at alkylating conditions in an alkylation zone in the presence of a catalytic composite to selectively form monoalkylated benzenes, said catalytic composite being a fluorided silica-alumina having a silica:alumina weight ratio of from about 1:1 to about 9:1 and containing from about 1 to about 6 weight percent fluorine; sulfonating the monoalkylated benzenes in a sulfonation zone with a sulfonating agent at sulfonation conditions to form sulfonic acids of the monoalkylated benzenes; and reacting said sulfonic acids with an aqueous solution of an alkali metal base to form the monoalkylbenzene alkali metal sulfonate.

9. The process as set forth in claim 1 in which said alkylation conditions include a temperature in the range of from about 80° to about 140° C., a pressure in the range of from about 200 to about 1,000 pounds per square inch gauge, and from about 5 to about 30 molar proportions of benzene for each molar proportion of linear monoolefin.

10. The process of claim 9 where the molar ratio of benzene to linear monoolefins is from about 8 to about 20.

11. The process of claim 9 where the temperature does not exceed 135° C.

12. The process of claim 8 where each monoolefin has from about 8 to about 16 carbon atoms.

13. The process of claim 12 where each monoolefin has from about 10 to about 14 carbon atoms.

14. The process of claim 8 where the catalyst has a silica to alumina weight ratio of from 65:35 to about 85:15.

15. The process of claim 8 where the catalyst contains from 1.5 to about 3.5 weight percent fluoride.

* * * * *